(12) United States Patent
Ramamoorthy et al.

(10) Patent No.: US 7,071,185 B2
(45) Date of Patent: Jul. 4, 2006

(54) 1,2,3,4,7,8-HEXAHYDRO-6H-[1,4]DIAZEPINO [6,7,1-IJ]QUINOLINE DERIVATIVES AS ANTIPSYCHOTIC AND ANTIOBESITY AGENTS

(75) Inventors: P. Sivaramakrishnan Ramamoorthy, Plainsboro, NJ (US); Robert E. McDevitt, Somerset, NJ (US)

(73) Assignee: Wyeth, Madison, NJ (US)

( * ) Notice: Subject to any disclaimer, the term of this patent is extended or adjusted under 35 U.S.C. 154(b) by 169 days.

(21) Appl. No.: 10/422,592

(22) Filed: Apr. 24, 2003

(65) Prior Publication Data

US 2004/0019040 A1 Jan. 29, 2004

Related U.S. Application Data

(60) Provisional application No. 60/376,153, filed on Apr. 25, 2002.

(51) Int. Cl.
A61P 25/00 (2006.01)
A61K 31/55 (2006.01)
C07D 243/00 (2006.01)

(52) U.S. Cl. ..................................... 514/219; 540/555
(58) Field of Classification Search ................ 514/219; 540/555

See application file for complete search history.

(56) References Cited

U.S. PATENT DOCUMENTS

| 3,158,619 | A | 11/1964 | Wagner | 260/310 |
|---|---|---|---|---|
| 3,235,564 | A | 2/1966 | Wagner | 260/327 |
| 3,296,252 | A | 1/1967 | Frey | 260/239.3 |
| 3,329,676 | A | 7/1967 | Bell | 260/239.3 |
| 3,335,134 | A | 8/1967 | Frey | 260/239.3 |
| 3,417,101 | A | 12/1968 | Bell | 260/328 |
| 3,466,274 | A | 9/1969 | Ridder | 260/239 |
| 3,714,149 | A | 1/1973 | Hester | 260/239.3 T |
| 3,914,250 | A | 10/1975 | Kim | 260/315 |
| 4,880,814 | A | 11/1989 | Chu | 546/123 |
| 4,997,831 | A | 3/1991 | Bays | 514/211 |
| 5,045,545 | A | 9/1991 | Bays | 514/284 |
| 5,834,454 | A | 11/1998 | Kitano et al. | 514/183 |
| 6,414,144 | B1 | 7/2002 | Welmaker | 540/555 |
| 6,503,900 | B1 | 1/2003 | Sabb et al. | 514/219 |
| 2002/0055504 | A1 | 5/2002 | Chan | 514/219 |
| 2002/0058689 | A1 | 5/2002 | Welmaker | 514/411 |
| 2002/0062022 | A1 | 5/2002 | Sabb | 540/556 |
| 2002/0107242 | A1 | 8/2002 | Sabb et al. | 514/219 |
| 2002/0119966 | A1 | 8/2002 | Sabb et al. | 514/219 |
| 2002/0128261 | A1 | 9/2002 | Sabb et al. | 514/219 |
| 2002/0173503 | A1 | 11/2002 | Robichaud et al. | 514/211.1 |
| 2003/0050300 | A1 | 3/2003 | McWhorter, Jr. | 514/211.1 |
| 2004/0009970 | A1 | 1/2004 | Ramamoorthy et al. | 514/220 |
| 2004/0034005 | A1 | 2/2004 | Gao et al. | 514/183 |

FOREIGN PATENT DOCUMENTS

| EP | 0 344 015 A2 | 11/1989 |
|---|---|---|
| EP | 0 357 417 A1 | 3/1990 |
| JP | 02-040379 | 2/1990 |
| JP | 10-237073 | 9/1998 |
| JP | 2001-89461 | 4/2001 |
| SU | 930902 | 11/1982 |
| WO | WO 90/15058 A1 | 12/1990 |
| WO | WO 96/29316 | 9/1996 |
| WO | WO 97/30999 A1 | 8/1997 |
| WO | WO 97/31000 A1 | 8/1997 |
| WO | WO 99/66934 A1 | 12/1999 |
| WO | WO 99/67219 A1 | 12/1999 |
| WO | WO 00/35922 | 6/2000 |
| WO | WO 00/40226 A2 | 7/2000 |
| WO | WO 00/64899 A1 | 11/2000 |
| WO | WO 00/77002 A1 | 12/2000 |
| WO | WO 01/12602 A1 | 2/2001 |
| WO | WO 01/12603 A1 | 2/2001 |
| WO | WO 01/64246 A2 | 9/2001 |
| WO | WO 02/08186 | 1/2002 |
| WO | WO 02/36596 A2 | 5/2002 |
| WO | WO 02/42304 A2 | 5/2002 |
| WO | WO 02/059124 A2 | 8/2002 |
| WO | WO 02/059129 A1 | 8/2002 |

OTHER PUBLICATIONS

Gregory E. Martin et al., J. Med. Chem., 32, 1052-1056 (1989).
J.L. Browning et al., Society for Neuroscience Abstracts, 25(2), 2075, Abstract 830.12, (1999).
Jackson B. Hester et al., J. Med. Chem., 13,827-835 (1970).
Dong H. Kim, J. Heterocycl. Chem., 13(6), 1187-1192 (1976).
H.P. Haerter et al., Chimia, 30, 50-52 (1976).

(Continued)

*Primary Examiner*—Brenda Coleman
(74) *Attorney, Agent, or Firm*—Kimberly R. Hild

(57) ABSTRACT

Compounds of Formula I or a pharmaceutically acceptable salt thereof are provided:

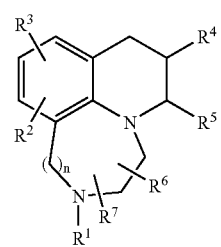

where $R^1$ through $R^7$ are defined herein. The compounds of Formula I are 5HT2c agonists or partial agonists, and are useful for treating a variety of disorders.

22 Claims, No Drawings

OTHER PUBLICATIONS

Oliver H. Lowry et al., J. Biol. Chem., 193, 265-275 (1951).
Samuel H. Wilen, et al., Tetrahedron, 33, 2725-2736 (1977).
Shunji Naruto et al., Tetrahedron Letters, 39, 3399-3402 (1975).
Giuseppe Digiovanni et al., Synapse, 35, 53-61 (2000).
Vincenzo Dimatteo et al., Neuropharmacology, 37, 265-272 (1998).
Vincenzo Dimatteo, et al., Neuropharmacology, 38, 1195-1205 (1999).
M.J. Millan et al., Neuropharmacology, 37, 953-955 (1998).
Prakash S. Masand, Exp. Opin. Pharmacother, 1(3), 377-389 (2000).
David B. Allison et al., Am. J. Psychiatry, 156(11), 1686-1696 (1999).
P.J. Cowan et al., Human Psychopharmacology, 10, 385-391 (1995).
A. Schotte et al., Psychopharmacology, 124, 57-73 (1996).
Susan H. Fox et al., Experimental Neurology, 151, 35-49 (1998).
R. Whitaker, Spectrum, 2, 1-12 (2000).
A.N. Grinev et al., Chem. Heterocycl. Compd., 19(9), 959-961 (1983).
A.N. Grinev et al., Chem. Heterocycl. Compd., 19(12), 1312-1315 (1983).
E.V. Lamanova et al., Pharm. Chem., J., 23(2), 113-115 (1989).
D.H. Kim et al., Journal of Medicinal Chemistry, 20(2), 209-212 (1977).
L. Toscano et al., J. Heterocyclic Chem., 13, 475-480 (1976).
A. Katritzky et al., Synthesis, 10, 1487-1490 (1998).
F. Gatta et al., Edizione Scientifica, 30(8), 631-641 (1975), structures only.
W. Lopes et al., Journal of Brazilian Chemical Society, 4(1), 34-39 (1993).
S. Rosenzweig-Lipson et al., The FASEB Journal, 14, A1321 (2000).

1,2,3,4,7,8-HEXAHYDRO-6H-[1,4]DIAZEPINO[6,7,1-IJ]QUINOLINE DERIVATIVES AS ANTIPSYCHOTIC AND ANTIOBESITY AGENTS

CROSS REFERENCE TO RELATED APPLICATIONS

This application claims the benefit under 35 U.S.C. §119(e) to U.S. provisional application Ser. No. 60/376,153 filed Apr. 25, 2002, which is hereby incorporated by reference in its entirety.

BACKGROUND OF THE INVENTION

Schizophrenia affects approximately 5 million people. At present, the most widespread treatments for schizophrenia are the 'atypical' antipsychotics, which combine dopamine ($D_2$) receptor antagonism with serotonin (5-$HT_{2A}$) receptor antagonism. Despite the reported advances in efficacy and side-effect liability of atypical antipsychotics over typical antipsychotics, these compounds do not adequately treat all of the symptoms of schizophrenia and are accompanied by problematic side effects including weight gain (Allison, D. B., et. al., Am. J. Psychiatry, 156: 1686–1696, 1999; Masand, P. S., Exp. Opin. Pharmacother. I: 377–389, 2000; Whitaker, R., Spectrum Life Sciences. Decision Resources. 2:1–9, 2000). Novel antipsychotics which are effective in treating the mood disorders or the cognitive impairments in schizophrenia without producing weight gain would represent a significant advance in the treatment of schizophrenia.

5-$HT_{2C}$ agonists and partial agonists represent a novel therapeutic approach toward the treatment of schizophrenia. Several lines of evidence support a role for 5-$HT_{2C}$ receptor agonism as a treatment for schizophrenia. Studies with 5-$HT_{2C}$ antagonists suggest that these compounds increase synaptic levels of dopamine and may be effective in animal models of Parkinson's disease (Di Matteo, V., et. al., Neuropharmacology 37: 265–272, 1998; Fox, S. H., et. al., Experimental Neurology 151: 35–49, 1998). Since the positive symptoms of schizophrenia are associated with increased levels of dopamine, compounds with actions opposite those of 5-$HT_{2C}$ antagonists such as 5-$HT_{2C}$ agonists and partial agonists should reduce levels of synaptic dopamine. Recent studies have demonstrated that 5-$HT_{2C}$ agonists decrease levels of dopamine in the prefrontal cortex and nucleus accumbens (Millan, M. J., et. al., Neuropharmacology 37: 953–955, 1998; Di Matteo, V., et. al., Neuropharmacology 38: 1195–1205, 1999; Di Giovanni, G., et. al., Synapse 35: 53–61, 2000), brain regions that are thought to mediate critical antipsychotic effects of drugs like clozapine. In contrast, 5-$HT_{2C}$ agonists do not decrease dopamine levels in the striatum, the brain region most closely associated with extrapyramidal side effects. In addition, a recent study demonstrates that 5-$HT_{2C}$ agonists decrease firing in the ventral tegmental area (VTA), but not in substantia nigra. The differential effects of 5-$HT_{2C}$ agonists in the mesolimbic pathway relative to the nigrostriatal pathway suggests that 5-$HT_{2C}$ agonists will have limbic selectivity and will be less likely to produce extrapyramidal side effects associated with typical antipsychotics.

Atypical antipsychotics bind with high affinity to 5-$HT_{2C}$ receptors and function as 5-$HT_{2C}$ receptor antagonists or inverse agonists. Weight gain is a problematic side effect associated with atypical antipsychotics such as clozapine and olanzapine and it has been suggested that 5-$HT_{2C}$ antagonism is responsible for the increased weight gain. Conversely, stimulation of the 5-$HT_{2C}$ receptor is known to result in decreased food intake and body weight (Walsh et. al., Psychopharmacology 124: 57–73, 1996; Cowen, P. J., et. al., Human Psychopharmacology 10: 385–391, 1995; Rosenzweig-Lipson, S., et. al., ASPET abstract, 2000). As a result, 5-$HT_{2C}$ agonists and partial agonists will be less likely to produce the body weight increases associated with current atypical antipsychotics. Indeed, 5-$HT_{2C}$ agonists and partial agonists are of great interest for the treatment of obesity, a medical disorder characterized by an excess of body fat or adipose tissue and associated with such comorbidities as Type II diabetes, cardiovascular disease, hypertension, hyperlipidemia, stroke, osteoarthritis, sleep apnea, gall bladder disease, gout, some cancers, some infertility, and early mortality.

SUMMARY OF THE INVENTION

In one embodiment, the present invention provides compounds of Formula I

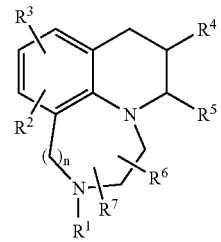

I where:

$R^1$ is hydrogen or alkyl of 1 to 6 carbon atoms;

$R^2$ and $R^3$ are each, independently, hydrogen, hydroxy, alkyl of 1–6 carbon atoms, alkoxy of 1–6 carbon atoms, halogen, carboxamido, carboalkoxy of two to six carbon atoms, perfluoroalkyl of 1–6 carbon atoms, cyano, alkanesulfonamido of 1–6 carbon atoms, alkanesulfonyl of 1–6 carbon atoms, alkanamido of 1–6 carbon atoms, amino, alkylamino of 1–6 carbon atoms, dialkylamino of 1–6 carbon atoms per alkyl moiety, perfluoroalkoxy of 1–6 carbon atoms, alkanoyloxy of 2 to 6 carbon atoms, alkanoyl of 2 to 6 carbon atoms, aroyl of 6 to 8 carbon atoms, aryl of 5 to 7 carbon atoms, a $C_6$ to $C_{13}$ alkylaryl group having 5 to 7 carbon atoms in the aryl moiety, a 5 to 7 membered heteroaryl group, or a 6 to 13 membered alkylheteroaryl group having 5 to 7 members in the heteroaryl moiety, wherein any $R^2$ or $R^3$ substituent having an aryl or heteroaryl moiety may optionally be substituted on the aryl or heteroaryl moiety with 1 to 3 substituents independently selected from a halogen atom, a $C_1$–$C_6$ alkyl group, or a $C_1$–$C_6$ alkoxy group;

$R^4$ and $R^5$ are, independently, hydrogen or alkyl of 1 to 6 carbon atoms, or $R^4$ and $R^5$, taken together with the carbons to which they are attached, form a cyclic moiety selected from a cycloalkane of 4 to 8 carbon atoms, cycloalkene of 4 to 8 carbon atoms, bridged bicyclic alkane of 5 to 10 carbon atoms, bridged bicyclic alkene of 5 to 10 carbon atoms, pyran or thiopyran in which the sulfur atom is optionally oxidized to the sulfoxide or sulfone, wherein the cyclic moiety formed by $R^4$ and $R^5$ may optionally be substituted with 1 to 3 substituents independently selected from a halogen atom, a $C_1$–$C_6$ alkyl group, or a $C_1$–$C_6$ alkoxy group;

$R^6$ and $R^7$ are each, independently, hydrogen or alkyl of 1 to 6 carbon atoms; and n is 1 or 2; or a pharmaceutically acceptable salt thereof.

In another embodiment of the present invention, a method of treating a mammal suffering from a condition selected from schizophrenia, schizophreniform disorder, schizoaffective disorder, delusional disorder, substance-induced psychotic disorder, L-DOPA-induced psychosis, psychosis associated with Alzheimer's dementia, psychosis associated with Parkinson's disease, psychosis associated with Lewy body disease, dementia, memory deficit, intellectual deficit associated with Alzheimer's disease, bipolar disorders, depressive disorders, mood episodes, anxiety disorders, adjustment disorders, eating disorders, epilepsy, sleep disorders, migraines, sexual dysfunction, gastrointestinal disorders, obesity, or a central nervous system deficiency associated with trauma, stroke, or spinal cord injury is provided that includes administering to the mammal at least one compound of Formula I or a pharmaceutically acceptable salt thereof.

In yet another embodiment of the present invention, a pharmaceutical composition is provided that contains at least one compound of Formula I and at least one pharmaceutically acceptable carrier or excipient.

DETAILED DESCRIPTION OF INVENTION

This invention provides compounds of Formula I

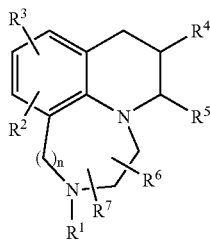

I where $R^1$ is hydrogen or alkyl of 1 to 6 carbon atoms;

$R^2$ and $R^3$ are each, independently, hydrogen, hydroxy, alkyl of 1–6 carbon atoms, alkoxy of 1–6 carbon atoms, halogen, carboxamido, carboalkoxy of two to six carbon atoms, perfluoroalkyl of 1–6 carbon atoms, cyano, alkanesulfonamido of 1–6 carbon atoms, alkanesulfonyl of 1–6 carbon atoms, alkanamido of 1–6 carbon atoms, amino, alkylamino of 1–6 carbon atoms, dialkylamino of 1–6 carbon atoms per alkyl moiety, perfluoroalkoxy of 1–6 carbon atoms, alkanoyloxy of 2 to 6 carbon atoms, alkanoyl of 2 to 6 carbon atoms, aroyl of 6 to 8 carbon atoms, aryl of 5 to 7 carbon atoms, a $C_6$ to $C_{13}$ alkylaryl group having 5 to 7 carbon atoms in the aryl moiety, a 5 to 7 membered heteroaryl group, or a 6 to 13 membered alkylheteroaryl group having 5 to 7 members in the heteroaryl moiety, wherein any $R^2$ or $R^3$ substituent having an aryl or heteroaryl moiety may optionally be substituted on the aryl or heteroaryl moiety with 1 to 3 substituents independently selected from a halogen atom, a $C_1$–$C_6$ alkyl group, or a $C_1$–$C_6$ alkoxy group;

$R^4$ and $R^5$ are, independently, hydrogen or alkyl of 1 to 6 carbon atoms, or $R^4$ and $R^5$, taken together with the carbons to which they are attached, form a cyclic moiety selected from a cycloalkane of 4 to 8 carbon atoms, cycloalkene of 4 to 8 carbon atoms, bridged bicyclic alkane of 5 to 10 carbon atoms, bridged bicyclic alkene of 5 to 10 carbon atoms, pyran or thiopyran in which the sulfur atom is optionally oxidized to the sulfoxide or sulfone, wherein the cyclic moiety formed by $R^4$ and $R^5$ may optionally be substituted with 1 to 3 substituents independently selected from a halogen atom, a $C_1$–$C_6$ alkyl group, or a $C_1$–$C_6$ alkoxy group;

$R^6$ and $R^7$ are each, independently, hydrogen or alkyl of 1 to 6 carbon atoms; and n is 1 or 2;

and pharmaceutically acceptable salts thereof.

In some preferred embodiments of the invention $R^2$ is hydrogen, halogen, cyano, perfluoroalkyl of 1 to 3 carbon atoms, alkyl of 1 to 6 carbon atoms, alkoxy of 1 to 6 carbon atoms, alkanoyl of 2 to 6 carbon atoms, or alkanesulfonyl of 1 to 6 carbon atoms or aryl of 5 to 7 carbon atoms. More preferably, $R^2$ is hydrogen, halogen, cyano, alkoxy of 1 to 3 carbon atoms, phenyl or trifluoromethyl.

In other preferred embodiments of the invention $R^3$ is hydrogen, halogen, cyano, perfluoroalkyl of 1 to 3 carbon atoms, alkyl of 1 to 6 carbon atoms, alkoxy of 1 to 6 carbon atoms, alkanoyl of 2 to 6 carbon atoms, or alkanesulfonyl of 1 to 6 carbon atoms or aryl of 5 to 7 carbon atoms. More preferably, $R^3$ is hydrogen, halogen, cyano, alkoxy of 1 to 3 carbon atoms, phenyl or trifluoromethyl.

$R^4$ and $R^5$ are preferably taken together, along with the carbon atoms to which they are attached, to form a cycloalkane or cycloalkene moiety of 5 to 8 carbon atoms, where one or more of the carbon atoms are optionally substituted by alkyl of 1 to 4 carbon atoms, and more preferably a cycloalkane moiety of 5 to 7 carbon atoms.

$R^1$, $R^6$ and $R^7$ are preferably hydrogen.

n is preferably 1.

In still other preferred embodiments of the invention, $R^2$ and $R^3$ are independently selected from hydrogen, halo, trifluoromethyl, phenyl or alkoxy of 1 to 3 carbon atoms, $R^1$, $R^6$ and $R^7$ are each hydrogen, n is 1, and $R^4$ and $R^5$, taken together with the carbon atoms to which they are attached, form cyclopentane, cyclohexane or cycloheptane.

The compounds of this invention contain asymmetric carbon atoms and thus give rise to optical isomers and diastereoisomers. While shown without respect to stereochemistry in Formula I, the present invention includes such optical isomers and diastereoisomers; as well as the racemic and resolved, enantiomerically pure R and S stereoisomers; as well as other mixtures of the R and S stereoisomers and pharmaceutically acceptable salts thereof.

Where an enantiomer is preferred, it may, in some embodiments be provided substantially free of the corresponding enantiomer. Thus, an enantiomer substantially free of the corresponding enantiomer refers to a compound which is isolated or separated via separation techniques or prepared free of the corresponding enantiomer. "Substantially free," as used herein, means that the compound is made up of a significantly greater proportion of one enantiomer. In preferred embodiments the compound is made up of at least about 90% by weight of a preferred enantiomer. In other embodiments of the invention, the compound is made up of at least about 99% by weight of a preferred enantiomer. Preferred enantiomers may be isolated from racemic mixtures by any method known to those skilled in the art, including high performance liquid chromatography (HPLC) and the formation and crystallization of chiral salts or prepared by methods described herein. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, IN 1972).

Alkyl, as used herein, refers to an aliphatic hydrocarbon chain and includes, but is not limited to, straight and branched chains such as methyl, ethyl, n-propyl, isopropyl, n-butyl, isobutyl, sec-butyl, t-butyl, n-pentyl, isopentyl, neopentyl, n-hexyl, and isohexyl. Lower alkyl refers to alkyl having 1 to 3 carbon atoms.

Alkanamido, as used herein, refers to the group R—C(=O)—NH— where R is an alkyl group of 1 to 5 carbon atoms.

Alkanoyl, as used herein, refers to the group R—C(=O)— where R is an alkyl group of 1 to 5 carbon atoms.

Alkanoyloxy, as used herein, refers to the group R—C(=O)—O— where R is an alkyl group of 1 to 5 carbon atoms.

Alkanesulfonamido, as used herein, refers to the group R—S(O)$_2$—NH— where R is an alkyl group of 1 to 6 carbon atoms.

Alkanesulfonyl, as used herein, refers to the group R—S(O)$_2$— where R is an alkyl group of 1 to 6 carbon atoms.

Alkoxy, as used herein, refers to the group R—O— where R is an alkyl group of 1 to 6 carbon atoms.

Aryl, as used herein, refers to an aromatic 5- to 7-membered monocarbocyclic ring such as phenyl. Heteroaryl means an aromatic 5- to 7-membered carbon containing monocyclic ring having one to two heteroatoms which independently may be nitrogen, oxygen or sulfur. Groups containing aryl or heteroaryl moieties may optionally be substituted as defined herein or unsubstituted.

Aroyl, as used herein, refers to the group Ar—C(=O)— where Ar is aryl as defined above. For example, a $C_6$ to $C_8$ aroyl moiety refers to the group Ar—C(=O)— where Ar is an aromatic 5 to 7 membered carbocyclic ring.

Alkylaryl, as used herein refers to the group —R—Ar where Ar is aryl as defined above and R is an alkyl moiety having 1 to 6, preferably 1 to 4, and more preferably 1 to 3 carbon atoms. Examples of alkylaryl groups include benzyl, phenethyl, 3-phenylpropyl, and 4-phenyl butyl. Alkylheteroaryl, as used herein, refers to the group —R-hetAr where hetAr is heteroaryl as defined above and R is an alkyl moiety having 1 to 6, preferably 1 to 4, and more preferably 1 to 3 carbon atoms.

Carboxamido, as used herein, refers to the group $NH_2$—C(=O)—.

Carboalkoxy as used herein refers to the group R—O—C(=O)— where R is an alkyl group of 1 to 5 carbon atoms.

Halogen (or halo) as used herein refers to chlorine, bromine, fluorine and iodine.

Pharmaceutically acceptable salts, including mono- and bi-salts, are those derived from such organic and inorganic acids such as, but not limited to acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids.

Specific examples of compounds of Formula I include:

1,2,3,4,8,8a,9,10,11,11a-decahydro-cyclopenta[b][1,4]diazepino[6,7,1-ij]quinoline;

1,2,3,4,8a,9,10,11,12,12a,-decahydro-8H-[1,4]diazepino[6,7,1-de]acridine;

and pharmaceutically acceptable salts thereof.

Specific examples also include substantially enantiomerically pure compounds of the foregoing including:

cis-1,2,3,4,8,8a,9,10,11,11a-decahydro-cyclopenta[b][1,4]diazepino[6,7,1-ij]quinoline;

trans-1,2,3,4,8,8a,9,10,11,11a-decahydro-cyclopenta[b][1,4]diazepino[6,7,1-ij]quinoline;

cis-1,2,3,4,8a,9,10,11,12,12a,-decahydro-8H-[1,4]diazepino[6,7,1-de]acridine;

trans-1,2,3,4,8a,9,10,11,12,12a,-decahydro-8H-[1,4]diazepino[6,7,1-de]acridine;

and pharmaceutically acceptable salts thereof.

The compounds of this invention can be prepared according to the following schemes from commercially available starting materials or starting materials which can be prepared using literature procedures. Variables used are as defined for Formula I, unless otherwise noted.

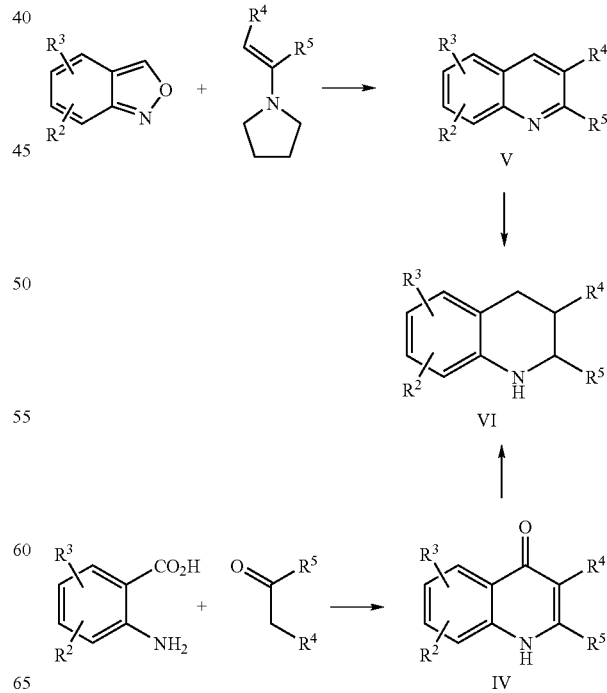

Scheme I

Scheme II

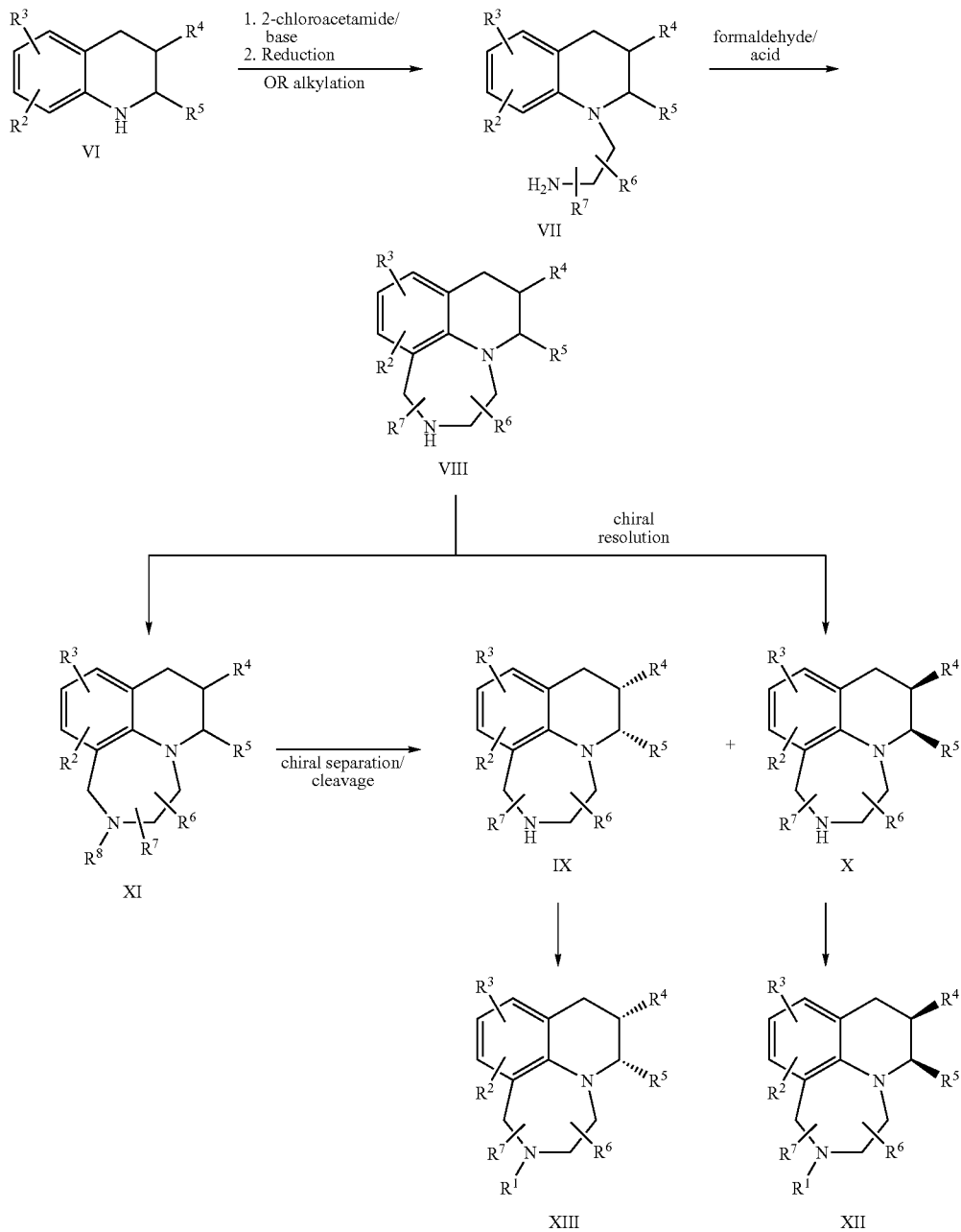

In Scheme I, two different methods are shown for the preparation of the intermediate VI. In the top reaction, a substituted benzoisoxazole can be reacted with the enamino derivative of a ketone in the presence of a premixed suspension of zinc powder and a Lewis acid such as titanium tetrachloride in an organic solvent such as THF. The resulting substituted quinolines V can be subjected to catalytic hydrogenolysis in the presence of a catalyst such as platinum oxide in an organic solvent such as methanol to give intermediate VI. An alternative method for the synthesis of VI is shown in the bottom equation of Scheme I. Treatment of anthranilic acids with thionyl chloride in a solvent such as benzene under refluxing conditions followed by the addition of a ketone yields intermediates IV. These can then be reduced by lithium aluminum hydride or sodium borohydride under acidic conditions to yield VI.

Scheme II exemplifies the conversion of VI to the final products. Intermediate VI can be alkylated, for instance with 2-chloroethyl amine under phase transfer conditions to yield VII. Alternatively, the side chain on VII can be installed via a two step procedure of alkylation with 2-chloroacetamide followed by reduction. Another alternative for forming VII from VI is a two step procedure where first a —CH$_2$—CN group is installed on the nitrogen of VI by the use of bromoacetonitrile in the presence of tetrabutylammonium iodide, potassium carbonate and a solvent such as THF, and then second, the cyano group is reduced by catalytic hydrogenation using for example rhodium on alumina in the presence of ethanol and ammonium hydroxide. VII is then subject to a pictet-spengler cyclization conditions with formaldehyde and a protic acid such as trifluoroacetic acid to yield VIII.

VIII can be resolved subsequently into its pure enantiomers by a chiral resolution to give compounds IX and X. Alternatively, VIII can be derivatised appropriately to give intermediate Xi, which can be separated by chiral chromatography and then subject to cleavage to give IX and X. Compounds IX and X can then be derivatised, for example, by alkylation, to give compounds XII and XIII which are also products of this invention.

Scheme III exemplifies an alternative reaction scheme for producing compounds of Formula I, where n is 2.

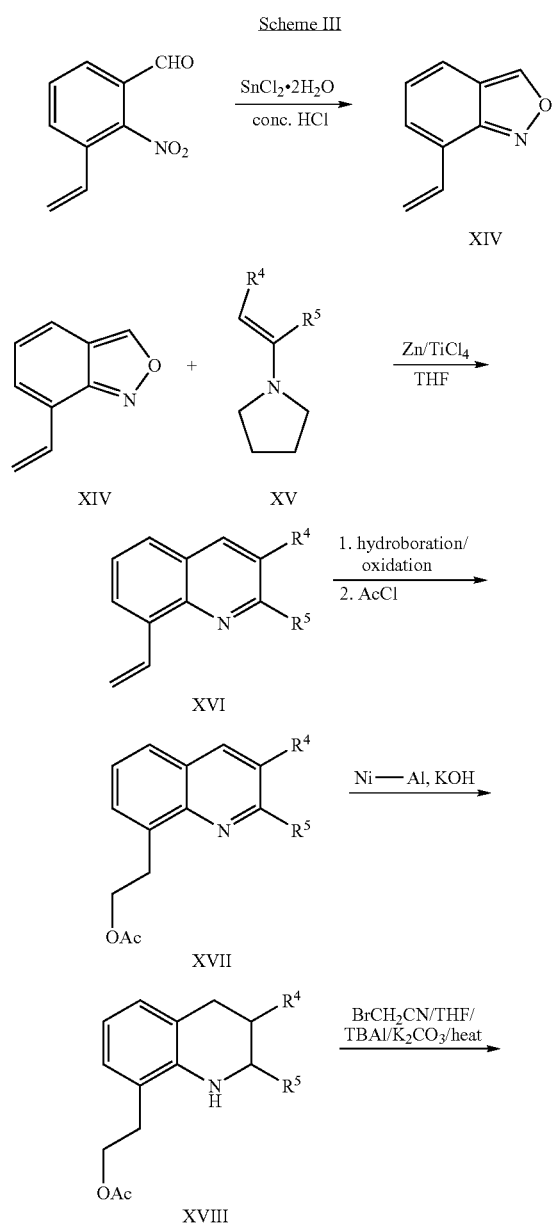

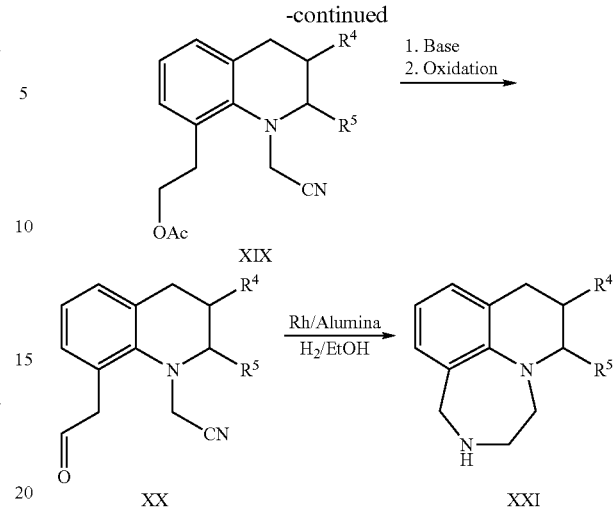

In Scheme III, 2-nitro-3-vinyl benzaldehyde is treated with a reducing agent such as tin dichloride in the presence of an acid such as conc. HCl to give 7-vinyl benzisoxazole XIV. Treatment of XIV with the enamino derivative of a ketone XV in the presence of a premixed suspension of zinc powder and a Lewis acid such as titanium tetrachloride in an organic solvent such as THF yields a quinoline compound XVI. Standard hydroboration/oxidation of the alkene followed by protection of the resulting alcohol as acetate yields XVII. Compound XVII is subjected to reduction by Ni—Al alloy in an organic solvent such as methanol in the presence of a strong base such as Aqueous KOH. The resulting tetrahydroquinoline compound XVIII can be alkylated under a variety of conditions to install the side-chain. One such condition involves alkylation with bromoacetonitrile and tetrabutylammonium iodide in the presence of a base such as potassium carbonate in an organic solvent such as THF to give the intermediate XIX. The acetate group of XIX can then be deprotected with a base such as potassium carbonate in an organic solvent such as methanol. The resulting alcohol is then subject to oxidation with an agent such as PDC to give the aldehyde XX. Hydrogenation of the nitrile moiety in XX with rhodium on alumina in the presence of hydrogen under pressure followed by ring closure to the aldehyde and subsequent reduction yields XXI which is a compound of Formula I where n is 2.

The compounds of this invention are agonists and partial agonists at the 2c subtype of brain serotonin receptors and are thus of interest for the treatment of mental disorders, including psychotic disorders such as schizophrenia including paranoid type, disorganized type, catatonic type, and undifferentiated type, schizophreniform disorder, schizoaffective disorder, delusional disorder, substance-induced psychotic disorder, and psychotic disorder not otherwise specified; L-DOPA-induced psychosis; psychosis associated with Alzheimer's dementia; psychosis associated with Parkinson's disease; psychosis associated with Lewy body disease; bipolar disorders such as bipolar I disorder, bipolar II disorder, and cyclothymic disorder; depressive disorders such as major depressive disorder, dysthymic disorder, substance-induced mood disorder, and depressive disorder not otherwise specified; mood episodes such as major depressive episode, manic episode, mixed episode, and hypomanic episode; anxiety disorders such as panic attack, agoraphobia, panic disorder, specific phobia, social phobia, obsessive compulsive disorder, posttraumatic stress disorder, acute stress disorder, generalized anxiety disorder, separation anxiety disorder, substance-induced anxiety disorder, and anxiety disorder not otherwise specified; adjustment disorders such as adjustment disorder with anxiety and/or depressed mood; intellectual deficit disorders such as dementia, Alzheimer's disease, and memory deficit; eating disorders (e.g., hyperphagia, bulimia or anorexia nervosa) and combinations of these mental disorders that may be present in a mammal. For example, mood disorders such as depressive disorders or bipolar disorders often accompany psychotic disorders such as schizophrenia. A more complete description of the aforementioned mental disorders can be found in the Diagnostic and Statistical Manual of Mental Disorders, 4$^{th}$ edition, Washington, D.C., American Psychiatric Association (1994).

The compounds of the present invention are also of interest for the treatment of epilepsy; migraines; sexual dysfunction; sleep disorders; gastrointestinal disorders, such as malfunction of gastrointestinal motility; and obesity, with its consequent comorbidities including Type II diabetes, cardiovascular disease, hypertension, hyperlipidemia, stroke, osteoarthritis, sleep apnea, gall bladder disease, gout, some cancers, some infertility, and early mortality. The compounds of the present invention can also be used to treat central nervous system deficiencies associated, for example, with trauma, stroke, and spinal cord injuries. The compounds of the present invention can therefore be used to improve or inhibit further degradation of central nervous system activity during or following the malady or trauma in question. Included in these improvements are maintenance or improvement in motor and motility skills, control, coordination and strength.

The ability of the compounds of this invention to act as $5HT_{2C}$ agonists and partial agonists was established using several standard pharmacological test procedures; the procedures used and results obtained are provided below. In the test procedures, 5-HT stands for 5-hydroxytryptamine, mCPP stands for meta-chlorophenylpiperazine, and DOI stands for 1-(2,5-dimethoxy-4-iodophenyl)isopropylamine.

$5HT_{2C}$ Receptor Binding Test Procedures

To evaluate high affinity for the $5HT_{2C}$ receptor, a CHO (Chinese Hamster Ovary) cell line transfected with the cDNA expressing the human 5-hydroxytryptamine$_{2C}$ (h5HT$_{2C}$) receptor was maintained in DMEM (Dulbecco's Modified Eagle Media) supplied with fetal calf serum, glutamine, and the markers: guaninephosphoribosyl transferase (GTP) and hypoxanthinethymidine (HT). The cells were allowed to grow to confluence in large culture dishes with intermediate changes of media and splitting. Upon reaching confluence, the cells were harvested by scraping. The harvested cells were suspended in half volume of fresh physiological phosphate buffered saline (PBS) solution and centrifuged at low speed (900×g). This operation was repeated once more. The collected cells were then homogenized with a polytron at setting #7 for 15 sec in ten volumes of 50 mM Tris.HCl, pH 7.4 and 0.5 mM EDTA. The homogenate was centrifuged at 900×g for 15 min to remove nuclear particles and other cell debris. The pellet was discarded and the supernatant fluid recentrifuged at 40,000×g for 30 min. The resulting pellet was resuspended in a small volume of Tris.HCl buffer and the tissue protein content was determined in aliquots of 10–25 microliter (μl) volumes. Bovine Serum Albumin (BSA) was used as the standard in the protein determination by the method of (Lowry et al, J. Biol. Chem., 193: 265, 1951). The volume of the suspended cell membranes was adjusted with 50 mM Tris.HCl buffer containing: 0.1% ascorbic acid, 10 mM pargyline and 4 mM CaCl$_2$ to give a tissue protein concentration of 1–2 mg per ml of suspension. The preparation membrane suspension (many times concentrated) was aliquoted in 1 ml volumes and stored at −70° C. until used in subsequent binding experiments.

Binding measurements were performed in a 96 well microtiter plate format, in a total volume of 200 μl. To each well was added: 60 μl of incubation buffer made in 50 mM Tris.HCl buffer, pH 7.4 and containing 4 mM CaCl$_2$; 20 μl of [$^{125}$I] DOI (S.A., 2200 Ci/mmol, NEN Life Science).

The dissociation constant, KD of [$^{125}$I] DOI at the human serotonin 5HT$_{2C}$ receptor was 0.4 nM by saturation binding with increasing concentrations of [$^{125}$I] DOI. The reaction was initiated by the final addition of 100.0 μl of tissue suspension containing 50 μg of receptor protein. Nonspecific binding is measured in the presence of 1 μM unlabeled DOI added in 20.0 μl volume. Test compounds were added in 20.0 ml. The mixture was incubated at room temperature for 60 min. The incubation was stopped by rapid filtration. The bound ligand-receptor complex was filtered off on a 96 well unifilter with a Packard® Filtermate 196 Harvester. The bound complex caught on the filter disk was dried in a vacuum oven heated to 60° C. and the radioactivity measured by liquid scintillation with 40 μl Microscint-20 scintillant in a Packard TopCount® equipped with six (6) photomultiplier detectors.

Specific binding is defined as the total radioactivity bound less the amount bound in the presence of 1 μM unlabeled DOI. Binding in the presence of varying concentrations of test drugs is expressed as percent of specific binding in the absence of drug. These results are then plotted as log % bound vs log concentration of test drug. Non linear regression analysis of data points yields both the IC50 and the Ki values of test compounds with 95% confidence limits. Alternatively, a linear regression line of decline of data points is plotted, from which the IC50 value can be read off the curve and the Ki value determined by solving the following equation:

$$Ki = \frac{IC50}{1 + L/KD}$$

where L is the concentration of the radioactive ligand used and the KD is the dissociation constant of the ligand for the receptor, both expressed in nM.

The following $K_i$'s (95% confidence interval) are provided for various reference compounds:

| | |
|---|---|
| Ritanserin | 2.0 (1.3–3.1) nM |
| Ketanserin | 94.8 (70.7–127.0) nM |
| Mianserin | 2.7 (1.9–3.8) nM |
| Clozapine | 23.2 (16.0–34.0) nM |
| Methiothepin | 4.6 (4.0–6.0) nM |
| Methysergide | 6.3 (4.6–8.6) nM |
| Loxapine | 33.0 (24.0–47.0) nM |
| mCPP | 6.5 (4.8–9.0) nM |
| DOI | 6.2 (4.9–8.0) nM |

Calcium Mobilization in Response to 5-HT$_{2C}$ Receptor Agonists

CHO cells stably expressing the human 5-HT$_{2C}$ receptor were cultured in Dulbecco's modified Eagle's medium (DMEM) supplemented with 10% fetal bovine serum and non-essential amino acids. Cells were plated at a density of 40K cells/well in 96-well clear-bottom black-wall plates 24 hr prior to the evaluation of 5-HT$_{2C}$ receptor stimulated calcium mobilization. For calcium studies cells were loaded with the calcium indicator dye Fluo-3-AM in Hank's buffered saline (HBS) for 60 minutes at 37° C. Cells were washed with HBS at room temperature and transferred to the fluorometric imaging plate reader (FLIPR, Molecular Devices, Sunnyvale, Calif.) for acquisition of calcium images. Excitation at 488 nm was achieved with an Argon ion laser and a 510–560 nm emission filter was used. Fluorescence images and relative intensities were captured at 1 second intervals and cells were stimulated by addition of agonist after 10 baseline measurements using the internal fluidics module of the FLIPR. An increase in fluorescence counts corresponds to an increase in intracellular calcium.

For the evaluation of agonist pharmacology the calcium changes in response to different concentrations of agonist were determined using a maximum minus minimum calculation of the raw fluorescence count data. Calcium changes were then expressed as a percentage of the response observed with a maximally effective concentration of 5-HT and EC50 values were estimated by non-linear regression analysis of the log-concentration % maximum 5-HT response curves using the 4-parameter logistic function.

The following EC$_{50}$'s and IC$_{50}$'s are provided for various reference compounds:

5-HT EC50 0.5 nM
DOI EC50 0.5 nM
mCPP EC50 5.4 nM

The results of the standard experimental test procedures described in the preceding paragraphs were as follows:

| Compound | 5-HT$_{2c}$ Affinity (DOI/Agonist binding) KI nM | 5-HT$_{2c}$ Function EC$_{50}$ (nM) | Emax (%) (5-HT, 100%) |
| --- | --- | --- | --- |
| Example 1, cis isomer | 118 | | |
| Example 1, trans isomer | 71 | | |
| Example 2, cis isomer | 511 | | |
| Example 2, trans isomer | 513 | | |

The compounds of this invention thus have affinity for and agonist or partial agonist activity at brain serotonin receptors. They are therefore of interest for the treatment of such CNS disorders, including psychotic disorders such as schizophrenia including paranoid type, disorganized type, catatonic type, and undifferentiated type, schizophreniform disorder, schizoaffective disorder, delusional disorder, substance-induced psychotic disorder, and psychotic disorder not otherwise specified; L-DOPA-induced psychosis; psychosis associated with Alzheimer's dementia; psychosis associated with Parkinson's disease; psychosis associated with Lewy body disease; bipolar disorders such as bipolar I disorder, bipolar II disorder, and cyclothymic disorder; depressive disorders such as major depressive disorder, dysthymic disorder, substance-induced mood disorder, and depressive disorder not otherwise specified; mood episodes such as major depressive episode, manic episode, mixed episode, and hypomanic episode; anxiety disorders such as panic attack, agoraphobia, panic disorder, specific phobia, social phobia, obsessive compulsive disorder, postraumatic stress disorder, acute stress disorder, generalized anxiety disorder, separation anxiety disorder, substance-induced anxiety disorder, and anxiety disorder not otherwise specified; adjustment disorders such as adjustment disorder with anxiety and/or depressed mood; intellectual deficit disorders such as dementia, Alzheimer's disease, and memory deficit; eating disorders (e.g., hyperphagia, bulimia or anorexia nervosa) and combinations of these mental disorders that may be present in a mammal. For example, mood disorders or episodes, such as depressive disorders or episodes often accompany psychotic disorders such as schizophrenia. A more complete description of the aforementioned mental disorders can be found in the Diagnostic and Statistical Manual of Mental Disorders, 4$^{th}$ edition, Washington, D.C., American Psychiatric Association (1994).

The compounds of the present invention are also of interest for the treatment of epilepsy; migraines; sexual dysfunction; sleep disorders; gastrointestinal disorders, such as malfunction of gastrointestinal motility; and obesity, with its consequent comorbidities including Type II diabetes, cardiovascular disease, hypertension, hyperlipidemia, stroke, osteoarthritis, sleep apnea, gall bladder disease, gout, some cancers, some infertility, and early mortality. The compounds of the present invention can also be used to treat central nervous system deficiencies associated, for example, with trauma, stroke, spinal cord injuries. The compounds of the present invention can therefore be used to improve or inhibit further degradation of central nervous system activity during or following the malady or trauma in question. Included in these improvements are maintenance or improvement in motor and motility skills, control, coordination and strength.

Thus the present invention provides methods of treating each of the maladies listed above in a mammal, preferably in a human, the methods comprising providing a therapeutically effective amount of a compound of this invention to the mammal in need thereof. By "treating", as used herein, it is meant partially or completely alleviating, inhibiting, preventing, ameliorating and/or relieving the disorder. For example, "treating" as used herein includes partially or completely alleviating, inhibiting or relieving the condition in question. "Mammals" as used herein refers to warm blooded vertebrate animals, such as humans. "Provide", as used herein, means either directly administering a compound or composition of the present invention, or administering a prodrug derivative or analog which will form an equivalent amount of the active compound or substance within the body.

Also encompassed by the present invention are pharmaceutical compositions for treating or controlling disease states or conditions of the central nervous system comprising at least one compound of Formula I, mixtures thereof, and or pharmaceutical salts thereof, and a pharmaceutically acceptable carrier therefore. Such compositions are prepared in accordance with acceptable pharmaceutical procedures, such as described in *Remingtons Pharmaceutical Sciences,* 17th edition, ed. Alfonoso R. Gennaro, Mack Publishing Company, Easton, Pa. (1985). Pharmaceutically acceptable carriers are those that are compatible with the other ingredients in the formulation and biologically acceptable.

The compounds of this invention may be administered orally or parenterally, neat or in combination with conventional pharmaceutical carriers, the proportion of which is determined by the solubility and chemical nature of the compound, chosen route of administration and standard pharmacological practice. The pharamceutical carrier may be solid or liquid.

Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be administered by, for example, intramuscular, intraperitoneal or subcutaneous injection. Sterile solutions can also be administered intravenously. Oral administration may be either liquid or solid composition form.

The compounds of this invention may be administered rectally or vaginally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermeable membrane covering a reservoir containing the active ingredient with or without a carrier, or a matrix containing the active ingredient. Other occlusive devices are known in the literature.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage requirements vary with the particular compositions employed, the route of administration, the severity of the symptoms presented and the particular subject being treated. Based on the results obtained in the standard pharmacological test procedures, projected daily dosages of active compound would be 0.02 µg/kg–750 µg/kg. Treatment will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based on experience with the individual subject treated. Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packaged powders, vials, ampules, pre-filled syringes or sachets containing liquids. The unit dosage form can be, for example, a capsule or tablet itself, or it can be the appropriate number of any such compositions in package form.

The present invention includes prodrugs of compounds of Formula I. Prodrug, as used herein, means a compound which is convertible in vivo by metabolic means (e.g. by hydrolysis) to a compound of Formula I. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113–191 (1991), Bundgaard, et al., Journal of Drug Delivery Reviews, 8:1–38(1992), Bundgaard, J. of Pharmaceutical Sciences, 77:285 et seq. (1988); and Higuchi and Stella (eds.) Prodrugs as Novel Drug Delivery Systems, American Chemical Society (1975).

EXAMPLES

The following provides the preparation of compounds representative of this invention.

Example 1

Cis and trans 1,2,3,4,8,8a,9,10,11,11a-decahydro-cyclopenta[b][1,4]diazepino[6,7,1-ij]quinoline Step 1—2,3-dihydro-1H-cyclopenta[b]quinoline Titanium tetrachloride (1.84 ml, 16.8 mmole) was added dropwise via syringe to a stirred suspension of Zn powder (1.1 g, 16.8 mmole) in freshly distilled dry THF (20 ml) at room temperature under nitrogen. When the addition was complete, the mixture was stirred at room temperature for 1.5 hours. To the suspension of low-valent titanium reagent formed, Anthranil (0.85 ml, 8.4 mmol) and 1-pyrrolidino-1-cyclopentene (4.9 ml, 33.6 mmol) dissolved in dry THF (15 ml) were added carefully. After 15 minutes, 20% NaOH (9 ml) is added with stirring and the organic phase was decanted off and dried over MgSO$_4$ and concentrated. Purification by flash chromatography (40% ethyl acetate/petroleum ether) gave the title compound as a brown oil, which was used directly in the next step.

Step 2—Cis and Trans 2,3,3a,4,9,9a-Hexahydro-1H-cyclopenta[b]quinoline

The title compound was prepared by catalytic hydrogenation of 2,3-dihydro-1H-cyclopenta[b]quinoline (0.5 g, 2.43 mmol) in the presence of PtO$_2$ and hydrogen (45 psi) in methanol (50 ml) to give the cis and trans isomers. Separation by flash chromatography (10–30% ethyl acetate/petroleum ether) gave the title compounds as light yellow solids (75%).

Cis 2,3,3a,4,9,9a-Hexahydro-1H-cyclopenta[b]quinoline:
mp 60–65° C.; Anal. calc. for C$_{12}$H$_{15}$N: C, 83.19; H, 8.73; N, 8.08. Found: C, 83.2; H, 8.45; N, 8.02. MS m/e (ES+): 174 (M+H). $^1$H NMR (DMSO-d$_6$) δ 6.85 (2H, m), 6.45 (1H, d, J=7.3 Hz), 6.40 (1H, t, J=7.2 Hz), 5.5 (1H, s), 3.55 (1H, m), 2.75 (1H, dd, J=15.5, 5.8 Hz), 2.37 (1H, dd, J=15.5, 5.8 Hz), 2.12 (1H,m), 1.75 (3H, m), 1.54 (2H, m) 1.28 (1H, m).

Trans 2,3,3a,4,9,9a-Hexahydro-1H-cyclopenta[b]quinoline:
mp 61° C.; Anal. calc. for C$_{12}$H$_{15}$N: C, 83.19; H, 8.73; N, 8.08. Found: C, 83.16; H, 8.44; N, 8. MS m/e (ES+): 174 (M+H). $^1$H NMR (DMSO-d$_6$) δ 6.86 (2H, m), 6.49 (2H, m), 5.86 (1H, s), 2.81 (2H, m), 2.56 (1H,m), 1.93 (2H,m), 1.76 (2H,m), 1.62 (1H, m), 1.36 (1H, m) 1.20 (1H, m).

Step 3—Cis and Trans(1,2,3,3a,9,9a-Hexahydro-cyclopenta[b]quinolin-4-yl)-acetonitrile To a stirred suspension of Cis 2,3,3a,4,9,9a-Hexahydro-1H-cyclopenta[b]quinoline (0.41 g, 2.35 mmole), K$_2$CO$_3$ (1.6 g, 11.8 mmole) and tetrabutyl ammonium Iodide (0.87 g, 2.35 mmole) in dry THF was added bromoacetonitrile (0.25 ml, 3.5 mmole). The reaction mixture was heated to 70° C. for 12 hours, then cooled to room temperature and filtered. The reaction was diluted with ethyl acetate and washed with water (25 mL) and brine (25 mL). The organic layer was dried with MgSO$_4$. Evaporation and flash chromatography (10% ethyl acetate/petroleum ether) gave 405 mg (81% yield) of the product as a gray brown solid. The same step 3 procedure was used to prepare the trans isomer except that trans 2,3,3a,4,9,9a-Hexahydro-1H-cyclopenta[b]quinoline was used instead of the cis isomer.

Cis(1,2,3,3a,9,9a-Hexahydro-cyclopenta[b]quinolin-4-yl)-acetonitrile:
mp 70–71° C. Anal. calc. for C$_{14}$H$_{16}$N$_2$: C, 79.21; H, 7.6; N, 13.2. Found: C, 78.97; H, 7.61; N, 13.17. MS m/e (ES+): 213 (M+H). $^1$H NMR (DMSO-d$_6$) δ 7.14 (1H, t, J=7.5 Hz), 7.05 (1H, d, J=7.2 Hz), 6.79 (1H, d, J=8.0 Hz), 6.74 (1H, t, J=7.3 Hz), 4.46 (2H, ABq, J=18 Hz, Δδ=0.13), 3.47 (1H, q, J=8.0 Hz), 2.65 (1H, dd, J=14, 5.2 Hz), 2.31 (1H, m), 2.23 (1H, m), 2.15 (1H, m), 1.94 (1H, m), 1.69 (1H, m) 1.44 (3H, m).

Trans(1,2,3,3a,9,9a-Hexahydro-cyclopenta[b]quinolin-4-yl)-acetonitrile:
Light gray solid (99%), mp 80–81° C.; Anal. calc. for C$_{14}$H$_{16}$N$_2$: C, 79.21; H, 7.6; N, 13.2. Found: C, 78.64 H, 7.37; N, 13.1. MS m/e (ES+): 213 (M+H). $^1$H NMR (DMSO-d$_6$) δ 7.11 (1H, t, J=7.5 Hz), 7.03 (1H, d, J=7.5 Hz), 6.95 (1H, d, J=8.2 Hz), 6.77 (1H, t, J=7.3 Hz), 4.80 (1H, d, J=18.5 Hz), 4.16 (1H, d, J=18.5 Hz), 2.86 (1H, dd, J=15.9, 4.9 Hz), 2.79 (1H, m), 2.63 (1H, m) 2.17 (1H, m), 1.99 (1H, m), 1.82 (3H, m), 1.39 (2H, m).

Step 4—Cis and trans 2-(1,2,3,3a,9,9a-Hexahydro-cyclopenta[b]quinolin-4-yl)-ethylamine Catalytic hydrogenation of Cis(1,2,3,3a,9,9a-Hexahydro-cyclopenta[b]quinolin-4-yl)-acetonitrile (0.23 g, 1.08 mmol) in the presence of 5% Rh on Alumina and hydrogen (45 psi) in a 1:1 mixture of ethanol : ammonium hydroxide (40 ml) afforded the title compound. The reaction mixture was filtered through celite concentrated in vacuo and purified by flash chromatography (10% 2N NH$_3$ in ethanol/dichloromethane) and converted to the HCl salt to give a white solid. The same step 4 procedure was used to prepare the trans isomer except that Trans (1,2,3,3a,9,9a-Hexahydro-cyclopenta[b]quinolin-4-yl)-acetonitrile was used instead of the cis isomer.

Cis 2-(1,2,3,3a,9,9a-Hexahydro-cyclopenta[b]quinolin-4-yl)-ethylamine:
(0.27 mg, 98%): mp 215–220° C.; Anal. calc. for C$_{14}$H$_{20}$N$_2$—HCl-0.25 H$_2$O: C, 65.36; H, 8.42; N, 10.88. Found: C, 65.35; H, 8.21; N, 10.63. MS m/e (ES+): 217 (M+H). $^1$H NMR (DMSO-d$_6$) δ 7.92 (3H, bs), 7.05 (1H, t, J=8.5 Hz), 6.99 (1H, d, J=7.0 Hz), 6.71 (1H, d, J=8.1 Hz), 6.61 (1H, t, J=7.3 Hz), 3.50 (3H, m), 2.95 (2H, m), 2.62 (1H, dd, J=15, 5.0 Hz), 2.30 (2H, m), 2.02 (1H, m), 1.85 (1H, m), 1.60 (1H, m) 1.35 (3H, m).

Trans 2-(1,2,3,3a,9,9a-Hexahydro-cyclopenta[b]quinolin-4-yl)-ethylamine
Off white solid (97%), mp 225–230° C.; Anal. calc. for C$_{14}$H$_{20}$N$_2$—HCl-0.75 H$_2$O: C, 63.15; H, 8.45; N, 10.52. Found: C, 63.53 H, 8.11; N, 10.41. MS m/e (ES+): 217 (M+H). $^1$H NMR (DMSO-d$_6$) δ 7.93 (3H, bs), 7.03 (1H, t, J=7.5 Hz), 6.94 (1H, d, J=7.2 Hz), 6.78 (1H, d, J=8.2 Hz), 6.61 (1H, t, J=7.3 Hz), 3.65 (1H, m), 2.93 (2H, m), 2.80 (2H, m), 2.59 (1H, m), 2.07 (1H, m) 1.78 (4H, m), 1.45 (1H, m), 1.27 (2H, m).

Step 5—Cis and Trans 1,2,3,4,8,8a,9,10,11,11a-decahydro-cyclopenta[b][1,4]diazepino[6,7,1-ij]quinoline A flask containing Cis 2-(1,2,3,3a,9,9a-Hexahydro-cyclopenta[b]quinolin-4-yl)-ethylamine (0.18 g, 0.84 mmol) and 0.07 ml of 37% aqueous formaldehyde in 2 ml of EtOH was treated with TFA (0.07 mL, 0.92 mmol) at room temperature for 1 hr. The mixture was concentrated under reduced pressure, and the residue was taken up in dichloromethane, washed with 1 N NaOH (15 mL), Brine (15 mL) and then dried with MgSO$_4$. Evaporation and flash chromatography (10% 2N NH$_3$ in ethanol/dichloromethane) afforded the title compound, which was converted to the HCl salt to give a brown solid (0.19 mg, 85%): The same step 5 procedure was used to prepare the trans isomer except that Trans 2-(1,2,3,3a,9,9a-Hexahydro-cyclopenta[b]quinolin-4-yl)-ethylamine was used instead of the cis isomer.

Cis 1,2,3,4,8,8a,9,10,11,11a-decahydro-cyclopenta[b][1,4]diazepino[6,7,1-ij]quinoline:
mp 180–190° C. (Decomposed); Anal. calc. for C$_{15}$H$_{20}$N$_2$—HCl-0.75 H$_2$O: C, 64.74; H, 8.15; N, 10.06. Found: C, 64.64; H, 8.18; N, 9.66. MS m/e (ES+): 229 (M+H). $^1$H NMR (DMSO-d$_6$) δ 9.23 (2H, bs), 7.01 (2H, t, J=8.1 Hz), 6.66 (1H, t, J=7.3 Hz), 4.20 (2H, ABq, J=14 Hz, Δδ=0.04), 3.78 (1H, m), 3.60 (1H, m), 3.40 (2H, m), 3.24 (1H, m), 2.67 (1H, m), 2.38 (2H, m), 1.91 (1H, m), 1.76 (1H, m), 1.54 (3H, m), 1.21 (1H, m).

Trans-1,2,3,4,8,8a,9,10,11,11a-decahydro-cyclopenta[b][1,4]diazapino[6,7,1-ij]quinoline:
Light green solid (72%), mp 190° C. (Decomposed); Anal. caic. for C$_{15}$H$_{20}$N$_2$—HCl-0.5 H$_2$O: C, 65.80; H, 8.10;

N, 10.23. Found: C, 65.50; H, 8.2; N, 9.78. MS m/e (ES+): 229 (M+H). $^1$H NMR (DMSO-d$_6$) δ 9.12 (2H, bs), 7.12 (1H, d, J=7.3 Hz), 7.03 (1H, d, J=7.3 Hz), 6.77 (1H, t, J=7.3 Hz), 4.32 (1H, d, J=14 Hz), 3.87 (1H, d, J=14 Hz), 3.41 (2H, m), 3.08 (2H, m), 2.81 (2H, m), 2.64 (1H, m), 2.11 (1H, m), 1.91 (1H, m), 1.77 (3H, m), 1.45 (1H, m), 1.29 (1H, m).

Example 2

Step 1—2,3-dihydro-1H-cyclohexa[b]quinoline

The title compound was prepared according to the procedure of Example 1 step 1 except that 1-pyrrolidino-1-cyclohexene was used as the dienophile to give a light brown oil (84%) and was used directly in the next step.

Step 2—Cis and Trans-1,2,3,4,4a,9,9a,10-octahydroacridine

The title compounds were prepared according to the procedure of Example 1 step 2, except that 2,3-dihydro-1H-cyclohexa[b]quinoline was hydrogenated instead of 2,3-dihydro-1H-cyclopenta[b]quinoline. Separation by flash chromatography (10–30% ethyl acetate/petroleum ether) gave the cis/trans isomers as white solids (74%).

Cis-1,2,3,4,4a,9,9a,10-octahydroacridine mp 69–70° C.; Anal. calc. for C$_{13}$H$_{17}$N: C, 83.37; H, 9.15; N, 7.48. Found: C, 83.06; H, 9.1; N, 7.43. MS m/e (ES+): 188 (M+H). $^1$H NMR (DMSO-d$_6$) δ 6.81 (2H, m), 6.43 (1H, d, J=7.5 Hz), 6.36 (1H, t, J=7.3 Hz), 5.44 (1H, s), 3.38 (1H, d, J=3.2 Hz), 2.79 (1H, dd, J=16.2, 5.5 Hz), 2.41 (1H, dd, J=16.2, 4 Hz), 1.85 (1H, t, J=3.8 Hz), 1.69 (1H, m), 1.53 (3H, m), 1.32 (4H, m).

Trans-1,2,3,4,4a,9,9a,10-octahydroacridine mp 78–79° C.; Anal. calc. for C$_{13}$H$_{17}$N: C, 83.37; H, 9.15; N, 7.48. Found: C, 82.94; H, 9.2; N, 7.31. MS m/e (ES+): 188 (M+H). $^1$H NMR (DMSO-d$_6$) δ 6.82 (2H, m), 6.41 (2H, m), 5.50 (1H, s), 2.75 (1H, m), 2.51 (1H, dd, J=16.0, 4.7 Hz), 2.37 (1H, dd, J=16.0, 12 Hz), 1.90 (1H, m), 1.81 (1H, d, J=6.3 Hz), 1.71 (2H, t, J=11.3 Hz), 1.31 (3H, m), 1.17 (1H, m), 0.95 (1H, m).

Step 3—Cis and Trans-2,3,4,4a,9,9a,-hexahydroacridin-10(1H)-ylacetonitrile

The title compounds were prepared according to the procedure of Example 1 step 3 except that Cis and Trans-1,2,3,4,4a,9,9a,10-octahydroacridine were used instead of Cis and Trans 2,3,3a,4,9,9a-Hexahydro-1H-cyclopenta[b]quinoline, respectively.

Cis-2,3,4,4a,9,9a,-hexahydroacridin-10(1H)-ylacetonitrile

Light green solid (86%): mp 86° C.; Anal. calc. for C$_{15}$H$_{18}$N$_2$: C, 79.61; H, 8.02; N, 12.38. Found: C, 79.29; H, 8.08; N, 12.4. MS m/e (ES+): 227 (M+H). $^1$H NMR (DMSO-d$_6$) δ 7.06 (1H, t, J=7.2 Hz), 6.98 (1H, d, J=7.3 Hz), 6.65 (2H, m), 4.48 (2H, ABq, J=16.2 Hz, Δδ=0.05), 3.34 (1H, m), 2.89 (1H, dd, J=16.2, 6.3 Hz), 2.49 (1H, m), 2.14 (1H,m), 1.81 (1H, m), 1.63 (3H, m), 1.44 (3H, m) 1.29 (1H, m).

Trans-2,3,4,4a,9,9a,-hexahydroacridin-10(1H)-ylacetonitrile

Light yellow solid (97%) mp 86° C.; Anal. calc. for C$_{15}$H$_{18}$N$_2$: C, 79.61; H, 8.02; N, 12.38. Found: C, 78.95; H, 8.19; N, 12.18. MS m/e (ES+): 227 (M+H). $^1$H NMR (DMSO-d$_6$) δ 7.03 (1H, t, J=7.3 Hz), 6.90 (1H, d, J=7.3 Hz), 6.81 (1H, d, J=7.7 Hz), 6.65 (1H, t, J=7.3 Hz), 4.45 (2H, ABq, J=18.7 Hz, Δδ=0.32), 2.67 (1H, m), 2.54 (1H, dd, J=16, 4.2 Hz), 2.40 (1H, dd, J=5.8, 2.3 Hz), 2.26 (1H, m), 1.79 (2H, m), 1.63 (1H, m), 1.49 (1H, m) 1.27 (2H, m), 1.07 (2H, m).

Step 4—2-[(Cis) and (Trans)-2,3,4,4a,9,9a,-hexahydroacridin-10(1H)-yl]ethylamine The title compound was prepared according to the procedure of Example 1 step 4, except that Cis and Trans-2,3, 4,4a,9,9a,-hexahydroacridin-10(1H)-ylacetonitrile were used instead of Cis and Trans(1,2,3,3a,9,9a-Hexahydro-cyclopenta[b]quinolin-4-yl)-acetonitrile, respectively.

2-[(Cis)-2,3,4,4a,9,9a,-hexahydroacridin-10(1H)-yl]ethylamine:

Off white solid (96%): mp 205–210° C. Anal. calc. for C$_{15}$H$_{22}$N$_2$—HCl-0.25 H$_2$O: C, 66.41; H, 8.73; N, 10.32. Found: C, 65.25; H, 8.33; N, 10.11. MS m/e (ES+): 231 (M+H). $^1$H NMR (DMSO-d$_6$) δ 7.94 (3H, bs), 6.98 (1H, t, J=7.2 Hz), 6.92 (1H, d, J=7.3 Hz), 6.61 (1H, d, J=8.2 Hz), 6.51 (1H, t, J=7.3 Hz), 3.56 (1H, m), 3.42 (1 H, m), 3.22 (1H, m), 2.92 (3H,m), 2.42 (1H, dd, J=16.2, 5.0 Hz), 2.20 (1H, m), 1.56 (4H, m) 1.34 (2H, m), 1.26 (2H, m).

2-[(Trans)-2,3,4,4a,9,9a,-hexahydroacridin-10(1H)-yl]ethylamine:

Off white solid (85%) mp 102° C. Anal. calc. for C$_{15}$H$_{22}$N$_2$: C, 78.21; H, 9.63; N, 12.16. Found: C, 78.1; H, 9.63; N, 12.07. MS m/e (ES+): 231 (M+H). $^1$H NMR (DMSO-d$_6$) δ 6.90 (1H, t, J=8.3 Hz), 6.76 (1H, d, J=7.2 Hz), 6.60 (1H, d, J=8.2 Hz), 6.42 (1H, t, J=7.2 Hz), 3.27 (3H, m), 3.05 (1H, m), 2.69 (2H, m), 2.51 (1H, m), 2.32 (2H, m) 1.76 (1H,m), 1.62 (1H, m), 1.40 (2H, m), 1.27 (2H, m), 1.02 (2H, m).

Step 5—(Cis) and (Trans)-1,2,3,4,8a,9,10,11,12,12a,-decahydro-8H-[1,4]diazepino[6,7,1-de]acridine The title compound was prepared according to the procedure of Example 1 step 5, except that 2-[(Cis) and (Trans)-2,3,4,4a,9,9a,-hexahydroacridin-10(1H)-yl]ethylamine were used instead of Cis and Trans 2-(1,2,3,3a,9,9a-Hexahydro-cyclopenta[b]quinolin-4-yl)-ethylamine, respectively.

(Cis)-1,2,3,4,8a,9,10,11,12,12a,-decahydro-8H-[1,4]diazepino[6,7,1-de]acridine

Light green solid (77%): mp 150–155° C. Anal. calc. for C$_{16}$H$_{22}$N$_2$—HCl-0.75 H$_2$O: C, 65.74; H, 8.45; N, 9.58. Found: C, 65.74; H, 8.24; N, 9.22. MS m/e (ES+): 243 (M+H). $^1$H NMR (DMSO-d$_6$) δ 9.32 (1H, bs), 8.70 (1H, bs), 7.08 (1H, d, J=7.4 Hz), 6.80 (1H, d, J=6.8 Hz), 6.73 (1H, t, J=7.3 Hz), 4.20 (1H, d, J=12.1 Hz), 3.86 (1H, dd, J=13.5, 9.8 Hz), 3.44 (1H, m), 3.17 (1H, m), 3.01 (2H, d, J=10.9 Hz), 2.73 (1H, dd, J=16.4, 5.4 Hz), 2.53 (1H, dd, J=16.4, 7.0 Hz), 2.08 (1H, m), 1.37 (9H, m).

(Trans)-1,2,3,4,8a,9,10,11,12,12a,-decahydro-8H-[1,4]diazepino[6,7,1-de]acridine Light tan solid (69%) mp 95° C. Anal. calc. for C$_{16}$H$_{22}$N$_2$: C, 79.29; H, 9.15; N, 11.56. Found: C, 78.53; H, 9.15; N, 11.32. MS m/e (ES+): 243 (M+H). $^1$H NMR (DMSO-d$_6$) δ 6.84 (1H, d, J=7.3 Hz), 6.74 (1H, d, J=7.3 Hz), 6.54 (1H, t, J=7.3 Hz), 3.75 (1H, d, J=14 Hz), 3.36 (1H, d, J=14 Hz), 3.19 (1H, d, J=14 Hz), 2.94 (1H, d, J=12 Hz), 2.58 (4H, m), 2.38 (2H, m), 2.01 (1H, m), 1.79 (1H, d, J=12 Hz), 1.65 (2H, m), 1.24 (3H, m), 1.05 (2H, m).

What is claimed is:

1. A compound of Formula I

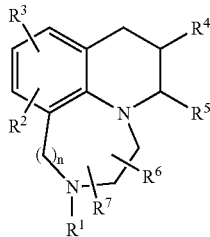

wherein:
R¹ is hydrogen or alkyl of 1 to 6 carbon atoms;
R² and R³ are each, independently, hydrogen, hydroxy, alkyl of 1–6 carbon atoms, alkoxy of 1–6 carbon atoms, halogen, carboxamido, carboalkoxy of two to six carbon atoms, perfluoroalkyl of 1–6 carbon atoms, cyano, alkanesulfonamido of 1–6 carbon atoms, alkanesulfonyl of 1–6 carbon atoms, alkanamido of 1–6 carbon atoms, amino, alkylamino of 1–6 carbon atoms, dialkylamino of 1–6 carbon atoms per alkyl moiety, perfluoroalkoxy of 1–6 carbon atoms, alkanoyloxy of 2 to 6 carbon atoms, alkanoyl of 2 to 6 carbon atoms, aroyl of 6 to 8 carbon atoms, aryl of 5 to 7 carbon atoms, a $C_6$ to $C_{13}$ alkylaryl group having 5 to 7 carbon atoms in the aryl moiety, a 5 to 7 membered heteroaryl group, or a 6 to 13 membered alkylheteroaryl group having 5 to 7 members in the heteroaryl moiety, wherein any R² or R³ substituent having an aryl or heteroaryl moiety may optionally be substituted on the aryl or heteroaryl moiety with 1 to 3 substituents independently selected from a halogen atom, a $C_1$–$C_6$ alkyl group, or a $C_1$–$C_6$ alkoxy group;
R⁴ and R⁵ are taken together with the carbon atoms to which they are attached, to form a cyclic moiety selected from a cycloalkane of 4 to 8 carbon atoms, cycloalkene of 4 to 8 carbon atoms, bridged bicyclic alkane of 5 to 10 carbon atoms, bridged bicyclic alkene of 5 to 10 carbon atoms, pyran or thiopyran in which the sulfur atom is optionally oxidized to the sulfoxide or sulfone, wherein the cyclic moiety formed by R⁴ and R⁵ may optionally be substituted with 1 to 3 substituents independently selected from a halogen atom, a $C_1$–$C_6$ alkyl group, or a $C_1$–$C_6$ alkoxy group;
R⁶ and R⁷ are each, independently, hydrogen or alkyl of 1 to 6 carbon atoms; and
n is 1;
or a pharmaceutically acceptable salt thereof.

2. The compound of claim 1 wherein, R² and R³ independently, are hydrogen, halogen, cyano, perfluoroalkyl of 1 to 3 carbon atoms, phenyl or alkoxy of 1 to 3 carbon atoms.

3. The compound of claim 1 wherein R⁴ and R⁵ are taken together, along with the carbon atoms to which they are attached, to form a cycloalkane or cycloalkene moiety of 5 to 8 carbon atoms, where one or more of the carbon atoms are optionally substituted by alkyl of 1 to 4 carbon atoms.

4. The compound of claim 1 wherein R⁴ and R⁵ are taken together, along with the carbon atoms to which they are attached, to form a cycloalkane moiety of 5 to 7 carbon atoms.

5. The compound of claim 1 wherein R¹, R⁶ and R⁷ are hydrogen.

6. The compound of claim 1 wherein R² and R³ are independently selected from hydrogen, halogen, trifluoromethyl, phenyl or alkoxy of 1 to 3 carbon atoms; R¹, R⁶ and R⁷ are each hydrogen; and R⁴ and R⁵, taken together with the carbon atoms to which they are attached, form cyclopentane, cyclohexane or cycloheptane.

7. The compound of claim 1 selected from
1,2,3,4,8,8a,9,10,11,11a-decahydro-cyclopenta[1,4]diazepino[6,7,1-ij]quinoline;
1,2,3,4,8a,9,10,11,12,12a,-decahydro-8H-[1,4]diazepino[6,7,1-de]acridine;
or pharmaceutically acceptable salts thereof.

8. The compound of claim 7 selected from
cis-1,2,3,4,8,8a,9,10,11,11a-decahydro-cyclopenta[b][1,4]diazepino[6,7,1-ij]quinoline;
trans-1,2,3,4,8,8a,9,10,11,11a-decahydro-cyclopenta[b][1,4]diazepino[6,7,1-ij]quinoline;
or pharmaceutically acceptable salts thereof.

9. The compound of claim 7 selected from
cis-1,2,3,4,8a,9,10,11,12,12a,-decahydro-8H-[1,4]diazepino[6,7,1-de]acridine;
trans-1,2,3,4,8a,9,10,11,12,12a,-decahydro-8H-[1,4]diazepino[6,7,1-de]acridine;
or pharmaceutically acceptable salts thereof.

10. A method of treating a mammal suffering from a condition selected from schizophrenia, schizophreniform disorder, schizoaffective disorder, delusional disorder, substance-induced psychotic disorder, L-DOPA-induced psychosis, psychosis associated with Alzheimer's dementia, psychosis associated with Parkinson's disease, psychosis associated with Lewy body disease, dementia, memory deficit, or intellectual deficit disorder associated with Alzheimer's disease comprising providing to the mammal suffering from the condition, a therapeutically effective amount of at least one compound of Formula I

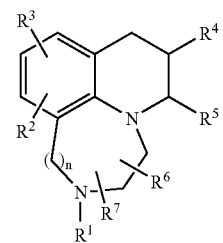

wherein:
R¹ is hydrogen or alkyl of 1 to 6 carbon atoms;
R² and R³ are each, independently, hydrogen, hydroxy, alkyl of 1–6 carbon atoms, alkoxy of 1–6 carbon atoms, halogen, carboxamido, carboalkoxy of two to six carbon atoms, perfluoroalkyl of 1–6 carbon atoms, cyano, alkanesulfonamido of 1–6 carbon atoms, alkanesulfonyl of 1–6 carbon atoms, alkanamido of 1–6 carbon atoms, amino, alkylamino of 1–6 carbon atoms, dialkylamino of 1–6 carbon atoms per alkyl moiety, perfluoroalkoxy of 1–6 carbon atoms, alkanoyloxy of 2 to 6 carbon atoms, alkanoyl of 2 to 6 carbon atoms, aroyl of 6 to 8 carbon atoms, aryl of 5 to 7 carbon atoms, a $C_6$ to $C_{13}$ alkylaryl group having 5 to 7 carbon atoms in the aryl moiety, a 5 to 7 membered heteroaryl group, or a 6 to 13 membered alkylheteroaryl group having 5 to 7 members in the heteroaryl moiety, wherein any $R^2$ or $R^3$ substituent having an aryl or heteroaryl moiety may optionally be substituted on the aryl or heteroaryl moiety with 1 to 3 substituents independently selected from a halogen atom, a $C_1$–$C_6$ alkyl group, or a $C_1$–$C_6$ alkoxy group;

$R^4$ and $R^5$ are taken together with the carbon atoms to which they are attached to form a cyclic moiety selected from a cycloalkane of 4 to 8 carbon atoms, cycloalkene of 4 to 8 carbon atoms, bridged bicyclic alkane of 5 to 10 carbon atoms, bridged bicyclic alkene of 5 to 10 carbon atoms, pyran or thiopyran in which the sulfur atom is optionally oxidized to the sulfoxide or sulfone, wherein the cyclic moiety formed by $R^4$ and $R^5$ may optionally be substituted with 1 to 3 substituents independently selected from a halogen atom, a $C_1$–$C_6$ alkyl group, or a $C_1$–$C_6$ alkoxy group;

$R^6$ and $R^7$ are each, independently, hydrogen or alkyl of 1 to 6 carbon atoms; and n is 1;

or a pharmaceutically acceptable salt thereof.

11. The method of claim 10 wherein the condition is schizophrenia.

12. The method of claim 10 wherein the mammal is human.

13. A method of treating a mammal suffering from a condition selected from bipolar disorders, depressive disorders, mood episodes, anxiety disorders, adjustment disorders, or eating disorders comprising providing to the mammal suffering from the condition, a therapeutically effective amount of at least one compound of Formula I

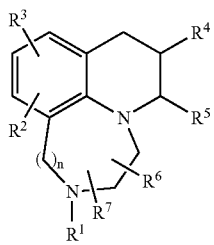

I wherein:

$R^1$ is hydrogen or alkyl of 1 to 6 carbon atoms;

$R^2$ and $R^3$ are each, independently, hydrogen, hydroxy, alkyl of 1–6 carbon atoms, alkoxy of 1–6 carbon atoms, halogen, carboxamido, carboalkoxy of two to six carbon atoms, perfluoroalkyl of 1–6 carbon atoms, cyano, alkanesulfonamido of 1–6 carbon atoms, alkanesulfonyl of 1–6 carbon atoms, alkanamido of 1–6 carbon atoms, amino, alkylamino of 1–6 carbon atoms, dialkylamino of 1–6 carbon atoms per alkyl moiety, perfluoroalkoxy of 1–6 carbon atoms, alkanoyloxy of 2 to 6 carbon atoms, alkanoyl of 2 to 6 carbon atoms, aroyl of 6 to 8 carbon atoms, aryl of 5 to 7 carbon atoms, a $C_6$ to $C_{13}$ alkylaryl group having 5 to 7 carbon atoms in the aryl moiety, a 5 to 7 membered heteroaryl group, or a 6 to 13 membered alkylheteroaryl group having 5 to 7 members in the heteroaryl moiety, wherein any $R^2$ or $R^3$ substituent having an aryl or heteroaryl moiety may optionally be substituted on the aryl or heteroaryl moiety with 1 to 3 substituents independently selected from a halogen atom, a $C_1$–$C_6$ alkyl group, or a $C_1$–$C_6$ alkoxy group;

$R^4$ and $R^5$ are taken together with the carbon atoms to which they are attached to form a cyclic moiety selected from a cycloalkane of 4 to 8 carbon atoms, cycloalkene of 4 to 8 carbon atoms, bridged bicyclic alkane of 5 to 10 carbon atoms, bridged bicyclic alkene of 5 to 10 carbon atoms, pyran or thiopyran in which the sulfur atom is optionally oxidized to the sulfoxide or sulfone, wherein the cyclic moiety formed by $R^4$ and $R^5$ may optionally be substituted with 1 to 3 substituents independently selected from a halogen atom, a $C_1$–$C_6$ alkyl group, or a $C_1$–$C_6$ alkoxy group;

$R^6$ and $R^7$ are each, independently, hydrogen or alkyl of 1 to 6 carbon atoms; and n is 1;

or a pharmaceutically acceptable salt thereof.

14. The method of claim 13 wherein the bipolar disorder is bipolar I disorder, bipolar II disorder, or cyclothymic disorder; the depressive disorder is major depressive disorder, dysthymic disorder, or substance-induced mood disorder; the mood episode is major depressive episode, manic episode, mixed episode, or hypomanic episode; the anxiety disorder is panic attack, agoraphobia, panic disorder, specific phobia, social phobia, obsessive compulsive disorder, posttraumatic stress disorder, acute stress disorder, generalized anxiety disorder, separation anxiety disorder, or substance-induced anxiety disorder.

15. The method of claim 13 wherein the condition is depressive disorder, bipolar disorder or mood episode.

16. The method of claim 13 wherein the mammal is human.

17. A method of treating a mammal suffering from a condition selected from epilepsy, sleep disorders, migraines, sexual dysfunction, gastrointestinal disorders, or obesity comprising providing to the mammal suffering from the condition, a therapeutically effective amount of at least one compound of Formula I

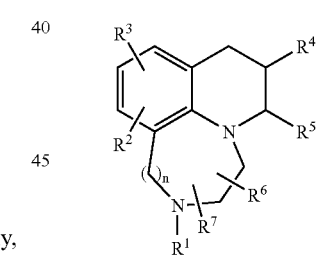

I wherein:

$R^1$ is hydrogen or alkyl of 1 to 6 carbon atoms;

$R^2$ and $R^3$ are each, independently, hydrogen, hydroxy, alkyl of 1–6 carbon atoms, alkoxy of 1–6 carbon atoms, halogen, carboxamido, carboalkoxy of two to six carbon atoms, perfluoroalkyl of 1–6 carbon atoms, cyano, alkanesulfonamido of 1–6 carbon atoms, alkanesulfonyl of 1–6 carbon atoms, alkanamido of 1–6 carbon atoms, amino, alkylamino of 1–6 carbon atoms, dialkylamino of 1–6 carbon atoms per alkyl moiety, perfluoroalkoxy of 1–6 carbon atoms, alkanoyloxy of 2 to 6 carbon atoms, alkanoyl of 2 to 6 carbon atoms, aroyl of 6 to 8 carbon atoms, aryl of 5 to 7 carbon atoms, a $C_6$ to $C_{13}$ alkylaryl group having 5 to 7 carbon atoms in the aryl moiety, a 5 to 7 membered heteroaryl group, or a 6 to 13 membered alkylheteroaryl group having 5 to 7 members in the heteroaryl moiety, wherein any $R^2$ or R[3] substituent having an aryl or heteroaryl moiety may optionally be substituted on the aryl or heteroaryl moiety with 1 to 3 substituents independently selected from a halogen atom, a $C_1$–$C_6$ alkyl group, or a $C_1$–$C_6$ alkoxy group;

R[4] and R[5] are taken together with the carbon atoms to which they are attached to form a cyclic moiety selected from a cycloalkane of 4 to 8 carbon atoms, cycloalkene of 4 to 8 carbon atoms, bridged bicyclic alkane of 5 to 10 carbon atoms, bridged bicyclic alkene of 5 to 10 carbon atoms, pyran or thiopyran in which the sulfur atom is optionally oxidized to the sulfoxide or sulfone, wherein the cyclic moiety formed by R[4] and R[5] may optionally be substituted with 1 to 3 substituents independently selected from a halogen atom, a $C_1$–$C_6$ alkyl group, or a $C_1$–$C_6$ alkoxy group;

R[6] and R[7] are each, independently, hydrogen or alkyl of 1 to 6 carbon atoms; and n is 1;

or a pharmaceutically acceptable salt thereof.

18. The method of claim 17 wherein the condition is obesity.

19. The method of claim 17 wherein the mammal is a human.

20. A method of treating a mammal suffering from a central nervous system deficiency associated with trauma, stroke, or spinal cord injury comprising providing to the mammal suffering from the condition, a therapeutically effective amount of at least one compound of Formula I

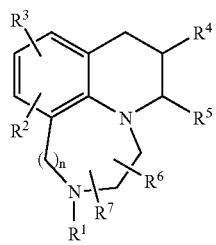

wherein:

R[1] is hydrogen or alkyl of 1 to 6 carbon atoms;

R[2] and R[3] are each, independently, hydrogen, hydroxy, alkyl of 1–6 carbon atoms, alkoxy of 1–6 carbon atoms, halogen, carboxamido, carboalkoxy of two to six carbon atoms, perfluoroalkyl of 1–6 carbon atoms, cyano, alkanesulfonamido of 1–6 carbon atoms, alkanesulfonyl of 1–6 carbon atoms, alkanamido of 1–6 carbon atoms, amino, alkylamino of 1–6 carbon atoms, dialkylamino of 1–6 carbon atoms per alkyl moiety, perfluoroalkoxy of 1–6 carbon atoms, alkanoyloxy of 2 to 6 carbon atoms, alkanoyl of 2 to 6 carbon atoms, aroyl of 6 to 8 carbon atoms, aryl of 5 to 7 carbon atoms, a $C_6$ to $C_{13}$ alkylaryl group having 5 to 7 carbon atoms in the aryl moiety, a 5 to 7 membered heteroaryl group, or a 6 to 13 membered alkylheteroaryl group having 5 to 7 members in the heteroaryl moiety, wherein any R[2] or R[3] substituent having an aryl or heteroaryl moiety may optionally be substituted on the aryl or heteroaryl moiety with 1 to 3 substituents independently selected from a halogen atom, a $C_1$–$C_6$ alkyl group, or a $C_1$–$C_6$ alkoxy group;

R[4] and R[5] are taken together with the carbon atoms to which they are attached to form a cyclic moiety selected from a cycloalkane of 4 to 8 carbon atoms, cycloalkene of 4 to 8 carbon atoms, bridged bicyclic alkane of 5 to 10 carbon atoms, bridged bicyclic alkene of 5 to 10 carbon atoms, pyran or thiopyran in which the sulfur atom is optionally oxidized to the sulfoxide or sulfone, wherein the cyclic moiety formed by R[4] and R[5] may optionally be substituted with 1 to 3 substituents independently selected from a halogen atom, a $C_1$–$C_6$ alkyl group, or a $C_1$–$C_6$ alkoxy group;

R[6] and R[7] are each, independently, hydrogen or alkyl of 1 to 6 carbon atoms; and n is 1;

or a pharmaceutically acceptable salt thereof.

21. A pharmaceutical composition comprising a) at least one compound of Formula I

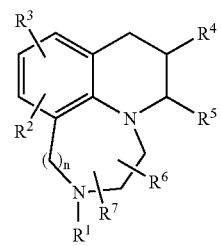

wherein:

R[1] is hydrogen or alkyl of 1 to 6 carbon atoms;

R[2] and R[3] are each, independently, hydrogen, hydroxy, alkyl of 1–6 carbon atoms, alkoxy of 1–6 carbon atoms, halogen, carboxamido, carboalkoxy of two to six carbon atoms, perfluoroalkyl of 1–6 carbon atoms, cyano, alkanesulfonamido of 1–6 carbon atoms, alkanesulfonyl of 1–6 carbon atoms, alkanamido of 1–6 carbon atoms, amino, alkylamino of 1–6 carbon atoms, dialkylamino of 1–6 carbon atoms per alkyl moiety, perfluoroalkoxy of 1–6 carbon atoms, alkanoyloxy of 2 to 6 carbon atoms, alkanoyl of 2 to 6 carbon atoms, aroyl of 6 to 8 carbon atoms, aryl of 5 to 7 carbon atoms, a $C_6$ to $C_{13}$ alkylaryl group having 5 to 7 carbon atoms in the aryl moiety, a 5 to 7 membered heteroaryl group, or a 6 to 13 membered alkylheteroaryl group having 5 to 7 members in the heteroaryl moiety, wherein any R[2] or R[3] substituent having an aryl or heteroaryl moiety may optionally be substituted on the aryl or heteroaryl moiety with 1 to 3 substituents independently selected from a halogen atom, a $C_1$–$C_6$ alkyl group, or a $C_1$–$C_6$ alkoxy group;

R[4] and R[5] are taken together with the carbon atoms to which they are attached to form a cyclic moiety selected from a cycloalkane of 4 to 8 carbon atoms, cycloalkene of 4 to 8 carbon atoms, bridged bicyclic alkane of 5 to 10 carbon atoms, bridged bicyclic alkene of 5 to 10 carbon atoms, pyran or thiopyran in which the sulfur atom is optionally oxidized to the sulfoxide or sulfone, wherein the cyclic moiety formed by R[4] and R[5] may optionally be substituted with 1 to 3 substituents independently selected from a halogen atom, a $C_1$–$C_6$ alkyl group, or a $C_1$–$C_6$ alkoxy group;

$R^6$ and $R^7$ are each, independently, hydrogen or alkyl of 1 to 6 carbon atoms; and n is 1;

or a pharmaceutically acceptable salt thereof; and b) at least one pharmaceutically acceptable carrier or excipient.

22. The composition of claim 21 wherein $R^2$ and $R^3$ are independently selected from hydrogen, halogen, trifluoromethyl, phenyl or alkoxy of 1 to 3 carbon atoms; $R^1$, $R^6$ and $R^7$ are each hydrogen; and $R^4$ and $R^5$, taken together with the carbon atoms to which they are attached, form cyclopentane, cyclohexane or cycloheptane.

* * * * *